US006812343B2

(12) United States Patent
Osuka

(10) Patent No.: US 6,812,343 B2
(45) Date of Patent: Nov. 2, 2004

(54) PORPHYRIN COMPOUNDS CONSISTING OF PORPHYRIN RINGS FUSED IN A SINGLE DIRECTION BY THREE BONDS, I.E., ONE MESO-MESO CARBON BOND AND TWO β-β CARBON BONDS AND PROCESS FOR THEIR SYNTHESIS

(75) Inventor: Atsuhiro Osuka, Shiga (JP)

(73) Assignee: Japan Science & Technology Agency, Saitama (JP)

( * ) Notice: Subject to any disclaimer, the term of this patent is extended or adjusted under 35 U.S.C. 154(b) by 0 days.

(21) Appl. No.: 10/343,920

(22) PCT Filed: Aug. 8, 2001

(86) PCT No.: PCT/JP01/06832

§ 371 (c)(1),
(2), (4) Date: Feb. 6, 2003

(87) PCT Pub. No.: WO02/14322

PCT Pub. Date: Feb. 21, 2002

(65) Prior Publication Data

US 2003/0187252 A1 Oct. 2, 2003

(30) Foreign Application Priority Data

Aug. 11, 2000 (JP) ........................................ 2000-243699

(51) Int. Cl.$^7$ ........................................... C07D 487/22
(52) U.S. Cl. ........................... 540/145; 534/15; 534/16; 540/121
(58) Field of Search .................................. 540/145, 121; 534/15, 16

(56) References Cited

FOREIGN PATENT DOCUMENTS

| JP | 2001-072745 | 3/2001 |
|----|-------------|--------|
| JP | 2001-294591 | 10/2001 |

OTHER PUBLICATIONS

Tsuda et al, Angew. Chem, Ind Ed, vol 39 (14) pp. 2549–2552 (2000).*

* cited by examiner

Primary Examiner—Richard L Raymond
(74) Attorney, Agent, or Firm—Sherman & Shalloway

(57) ABSTRACT

A porphyrin ring-fusion polymer which consists of two or more Zn(II)-porphyrin rings fused in a single direction and in which any two porphyrin rings adjacent to each other are fused by three covalent bonds, that is, one meso-meso carbon bond (i.e., one bond between meso-position carbon atoms) and two β—β carbon bonds (i.e., two bonds between β-position carbon atoms adjacent to the meso-position carbon atoms); a process for preparing the porphyrin ring-fusion polymer regioselectively by conducting the fusion reaction in an aromatic hydrocarbon solvent in the presence of a quinoline and Lewis acid containing rare earth element under reflux; and fused-ring porphyrin compound obtained by subjecting the porphyrin ring-fusion polymer to demetallization or replacement of the Zn atoms by other metal atoms.

10 Claims, 2 Drawing Sheets

PORPHYRIN COMPOUNDS CONSISTING OF PORPHYRIN RINGS FUSED IN A SINGLE DIRECTION BY THREE BONDS, I.E., ONE MESO-MESO CARBON BOND AND TWO β-β CARBON BONDS AND PROCESS FOR THEIR SYNTHESIS

This application is a 371 of PCT/JP01/06832, filed Aug. 8, 2001.

FIELD OF THE INVENTION

The present invention relates to a method for preparation of meso-meso, β—β, β—β, triply linked porphyrin arrays, represented by general formula 1, by oxidizing the corresponding meso-meso linked Zn(II) porphyrins, represented by general formula 2, with a selected combination of Lewis acid and quinone oxidant, and a method for preparation of meso-meso; β—β, β—β, triply porphyrin tetramers (general formula 1, n=2) from Zn(II) porphyrin monomers, represented by general formula 3 where $R^1$–$R^9$ are substituted and especially $R^2$, $R^5$, and $R^8$ are aryl groups, and $R^{10}$, $R^{11}$, and $R^{12}$ are unsubstituted. The meso-meso, β—β, β—β, triply linked Zn(II) porphyrin arrays exhibit remarkable planarity and exceptionally large electronic interactions as evidenced by their absorption and electronic properties.

BACK GROUND OF THE INVENTION

Porphyrins exhibit strong absorbance in the visible region, strong fluorescence and phosphorescence, and high electric conductivity, because the HOMO-LUMO gap is relatively small. Furthermore, porphyrins have an advantage to accommodate almost all metal ions in their cavities as a ligand and such metallations and peripheral substitutions enable the tuning of optical and electrochemical properties, thus providing a variety of compounds that can fulfill the required properties when used in functional materials and devices. In nature, porphyrins are responsible for various important functions in biological processes such as oxidation-reduction reactions in metabolism, photosynthesis, and respiration. With these backgrounds, prophyrin-based molecular systems such as energy-converting functional materials and bio-mimetic catalysts have been actively developed. Recently, considerable attention has been paid to multi-porphyrin systems from a viewpoint of their application as opto-electronic material. In this line, syntheses of porphyrin polymers or oligomers bearing long, rigid, planar, and thus the exploration of extensively π-conjugated electronic systems and new devices based on the strong absorbance in the visible region, strong fluorescence and phosphorescence, and small optical HOMO-LUMO energy gap have been actively attempted.

Among these, the present inventor has reported the synthesis of directly meso-meso linked linear porphyrin polymers (consisting of 300–400 porphyrin subuints) and discrete meso-meso linked porphyrin oligomers up to a 128 mer. In addition, he also proposed the possibility of the synthesis of fused porphyrin oligomers by linking two β- and β-positions directly through oxidation of meso-meso linked porphyrin arrays.

The linear meso-meso linked porphyrin arrays have been regarded to be a promising unit for the usage as optical wire and electric molecular wire in light of rod-like structure, large electronic interactions between the neighboring porphyrin that are sufficient to induce rapid non-coherent excitation energy transfer hopping, and lack of an energy sink that blocks the energy transfer cascade long the array. These properties are apparently induced from the directly linked and perpendicular conformation of the neighboring porphyrins. The perpendicular conformation, however, leads to the disruption of π-conjugation and therefore the electric conductivity of the meso-meso linked porphyrins is only modest. When the perpendicular meso-meso linked porphyrin arrays are converted into flat and coplanar arrays by linking twoβ—β, β—β bonds, we may reach to extensively π-conductive porphyrin arrays that will be very promising as a molecular wire in a realistic molecular scale.

The present inventor proposed the linearly fused porphyrin arrays bearing meso-β and meso-β double linkages as a more practical candidate for molecular wire. But such arrays are not sufficient for practical applications as optical wire and molecular wire in terms of the electronic interaction and molecular size.

Therefore, the present inventor proposed a new method of preparation of meso-meso, β—β, β—β triply directly linked porphyrin arrays that extend linearly to form a tape-shape porphyrin tape (JP2000-110157 application: JP Laid Open Pub. 2001-294591). However, this synthetic protocol was only applied to the preparation of the porphyrin tapes in which the number of the porphyrin was very limited, due to concurrent peripheral β-halogenations.

The object of the present invention is to explore porphrin-based more extensively π-conjugated network which realized much longer molecular length and more electron delocalization, hence providing conjugated porphyrin arrays that will be used as optical wire and electric conducting wire.

For the use as electric wire, it is desirable to minimize the HOMO-LUMO gap as small as possible. For this purpose, extensively conjugated porphyrin arrays consisting of many porphyrins are required. Accordingly, the second object of the present invention is to establish the effective method for synthesis of conjugated porphyrin arrays of very small HOMO-LUMO gap.

In the course of these studies, the present inventor have found that a new synthetic method for converting meso-meso linked meso,meso' phenyl capped Zn(II) porphyrin oligomers to meso-meso, β—β, β—β triply directly linked Zn(II) porphyrin oligomers with quinone oxidant in the presence of suitable Lewis acid in refluxing toluene or benzonitrile solution.

DISCLOSURE OF THE INVENTION

The first one of the present invention is meso-meso, β—β,β—β triply directly linked, so-called fused porphyrin oligomers represented by general formula 1.

General formula 1

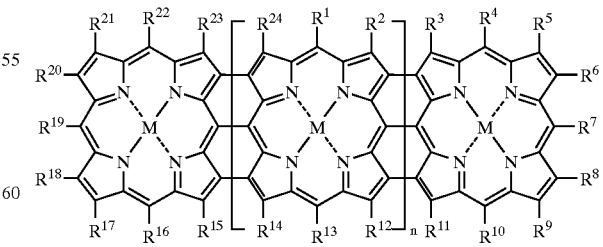

(wherein, $R^1$–$R^{24}$ are respectively selected independently from the group consisting of hydrogen, halogen, hydroxyl group, mercapto group, amino group, nitro group, cyano group, carboxyl group, sulfonic acid group, substituted or non-substituted alkyl group, substituted or non-substituted aryl group, substituted or non-substituted alkoxy group, substituted or non-substituted aryloxy group, substituted or non-substituted alkylthio group, substituted or non-substituted arylthio group, alkylamino group, substituted or non-substituted arylamino group, substituted or non-substituted carboxylate group, substituted or non-substituted carboxylic acid amino group, substituted or non-substituted sulfonate group, substituted or non-substituted sulfonamide group, substituted or non-substituted carbonyl group, substituted or non-substituted silyl group or substituted or non-substituted siloxy group, n is an integer bigger than 2, general formula 1 featuring the neighboring porphyrin rings are meso-meso, β—β, β—β, triply directly linked in a linear fashion from the meso-meso linked zn(II)-porphyrin oligomers represented by general formula 2, and the corresponding fused porphyrin free base oligomers (M=2H)) repared by demetalization of the above fused Zn(II) porphyrin oligomers, or the fused M(+m)-porphyrin oligomers by inserting other metal instead of Zn (wherein, M is a metal selected from above mentioned group of metal atoms except Zn, m is a possible ionic valence number of each metal), represented by general formula 1.

General formula 2

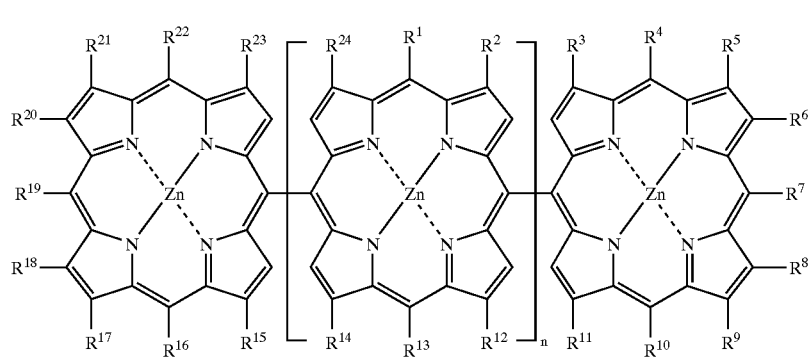

M is 2H or a complex replaced two hydrogen atoms of porphyrin ring with metal atom selected from the group of metal atoms of $A_n$. wherein metal atom group A is Zn, Mg, Ca, Sr, Ba, Sc, Y, La, Ce, Pr, Nd, Sm, Eu, Gd, Tb, Dy, Ho, Er, Tm, Yb, Lu, Ti, Zr, Hf, V, Nb, Ta, Th, U, Cr, Mo, W, Mn, Tc, Re, Fe, Ru, Os, Co, Rh, Ir, Ni, Pd, Pt, Cu, Ag, Au, Cd, Hg, Al, Ga, In, Ti, Si, Ge, Sn, Pb, As, Sb, and Bi.)

Desirably, the present invention is the above mentioned fused porphyrin oligomers, wherein in the above mentioned general formula 1, $R^1$, $R^4$, $R^{10}$, $R^{13}$, $R^{16}$, $R^{22}$ are selected independently from phenyl groups having substituent selected independently from alkyl group or alkoxy group of carbon number 1 or more, $R^7$ and $R^{19}$ are respectively selected independently from the group consisting of hydrogen, halogen, hydroxyl group, mercapto group, amino group, nitro group, cyano group, carboxyl group, sulfonic acid group, substituted or non-substituted alkyl group, substituted or non-substituted aryl group, substituted or non-substituted alkoxy group, substituted or non-substituted aryloxy group, substituted or non-substituted alkylthio group, substituted or non-substituted arylthio group, alkylamino group, substituted or non-substituted arylamino group, substituted or non-substituted carboxylate group, substituted or non-substituted carboxylic acid amino group, substituted or non-substituted sulfonate group, substituted or non-substituted sulfonamide group, substituted or non-substituted carbonyl group, substituted or non-substituted silyl group or substituted or non-substituted siloxy group.

More desirably, the present invention is the bove mentioned fused porphyrin oligomers, wherein in the above mentioned general formula 1, $R^1$, $R^4$, $R^{10}$, $R^{13}$, $R^{16}$, $R^{22}$ are the compound independently selected from the group consisting of 3,5-di-tertialbutylphenyl group or 3,5-di-octyloxyphenyl group.

The second one of the present invention is the method for synthesis of the fused Zn(II) porphyrin oligomres (n=0, or an integer bigger than 1 and M is Zn in above mentioned In the general formula 2, $R^1$–$R^{24}$ are same as to general formula 1, n is 0 or integer bigger than 1. In this synthetic method, the conversion from the meso-meso linked porphyrin oligomers to the fused porphyrin oligomers was carried out in solvent with quinone oxidants in the presence of suitable Lewis acid containing rare earth ion.

Desirably, the second one of the present invention is the method for synthesis of the fused Zn(Ii) porphyrin oligomers wherein $R^1$, $R^4$, $R^7$, $R^{10}$, $R^{13}$, $R^{16}$, $R^{19}$ and $R^{22}$ of the above mentioned general formula 1 are the phenyl group or the phenyl group substituted with substituents selected independently from alkyl group or alkoxy group of carbon number 1 or more, and is the method for synthesis of the fused porphyrin free base oligomers wherein M is 2H by demetallation of the said fused Zn(II) porphyrin oligomers, and the fused M(+m) porphyrin oligomers by inserting other metal instead of Zn (wherein, M is a metal selected from the above mentioned group of metal atoms except Zn, m is a possible ionic valence number of each metal). In this synthetic method, the conversion from the mesa-mesa linked porphyrin oligomers to the fused porphyrin oligomers was carried out in solvent with quinone oxidants in the presence of suitable Lewis acid containing rare earth ion.

The third one of the presefit invention is the method for synthesis of the mesa-mesa, β—β, β—β directly triply linked, so-called fused zn(II) porphyrin dimers, and their corresponding fused free base porphyrin dimers prepared by demetalization of the above fused Zn(II) porphyrin dimer, and the fused M(+m) porphyrin compound (wherein, M is a metal selected from above mentioned group of metal atoms except Zn, m is a possible ionic valence number of each metal), which are prepared by oxidative dimerization of a Zn(II) porphyrin monomer represented by general formula 3

General formula 3

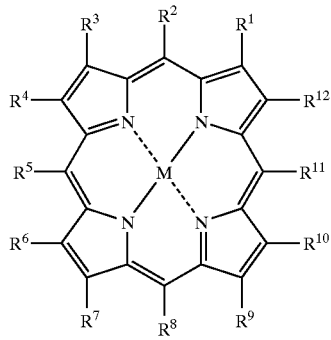

(wherein M is Zn, $R^{10}$–$R^{12}$ are hydrogen and $R^1$–$R^9$ are respectively selected independently from the group consisting of hydrogen, halogen, hydroxyl group, mercapto group, amino group, nitro group, cyano group, carboxyl. group, sulfonic acid group, substituted or non-substituted alkyl group, substituted or non-substituted aryl group, substituted or non-substituted alkoxy group, substituted or non-substituted aryloxy group, substituted or non-substituted alkylthio group, substituted or non-substituted arylthio group, alkylamino group, substituted or non-substituted arylamino group, substituted or non-substituted carboxylate group, substituted or non-substituted carboxylic acid amino group, substituted or non-substituted sulfonate group, substituted or non-substituted sulfonamide group, substituted or non-substituted carbonyl group, substituted or non-substituted silyl group or substituted or non-substituted siloxy group). The oxidative dimerization reaction is carried out in solvent with quinone oxidants in the presence of suitable Lewis acid containing rare earth ion.

Desirably, the third one of the present invention is the method for synthesis of the meso-meso, β—β, β—β directly triply linked, so-called fused Zn(II) porphyrin dimers, and the fused metal free porphyrin dimers prepared by demetalization of the above Zn(II)-porphyrin dimers, and the fused M(+m) porphyrin compound (wherein, M is a metal selected from above mentioned group of metal atoms except Zn, m is a possible ionic valency number of each metal) represented by general formula 3, wherein, $R^1$, $R^3$, $R^4$, $R^6$, $R^7$, $R^9$–$R^{12}$ are hydrogen, $R^2$, $R^5$ and $R^8$ of above mentioned general formula 3 are the phenyl group having substituent selected independently from alkyl group or alkoxy group of carbon number 1 or more.

More desirably, the third one of the present invention is the method for synthesis of the above mentioned fused Zn(II) porphyrin dimers, the above mentioned fused metal free porphyrin dimers prepared by demetalization of the above Zn(II)-porphyrin dimers, and the above mentioned fused M(+m)-porphyrin compound (wherein, M is a metal selected from above mentioned group of metal atoms except Zn, m is a possible ionic valence number of each metal), wherein the phenyl group having substituent selected independently from alkyl group or alkoxy group of carbon number 1 or more is the phenyl group whose 3, 5 positions are substituted by tertiary butyl group or octyloxy group, even more desirably, the third one of the present invention is the method for synthesis of the above mentioned fused metal free porphyrin dimers prepared by demetallation of the above fused Zn(II) porphyrin dimers and the corresponding fused M(+m) porphyrin compound (wherein, M is a metal selected from above mentioned group of metal atoms except Zn, m is a possible ionic valence number of each metal). The oxidative dimerization reaction is carried out under refluxing condition in aromatic hydrocarbon solvents in the presence of quinone oxidants selected from quinones and Lewis acids containing rare earth lanthanide element.

EXPLANATION OF INFRARED SPECTRA

Figure 1:
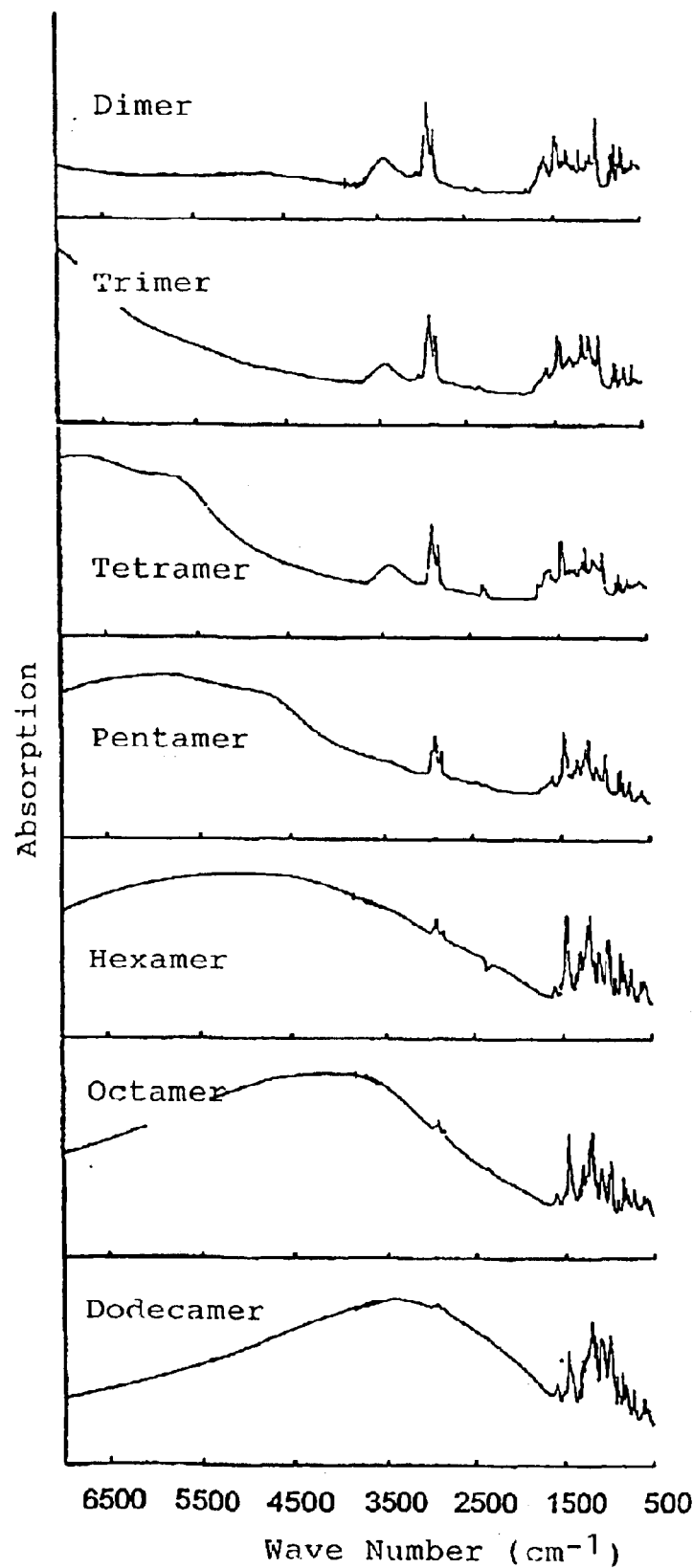
FIG. 1 shows the absorption spectra of the meso-meso, β—β, β—β triply directly linked, so-called fused Zn(II) porphyrin oligomers up to 12-mer that are the present invention.
Figure 2:
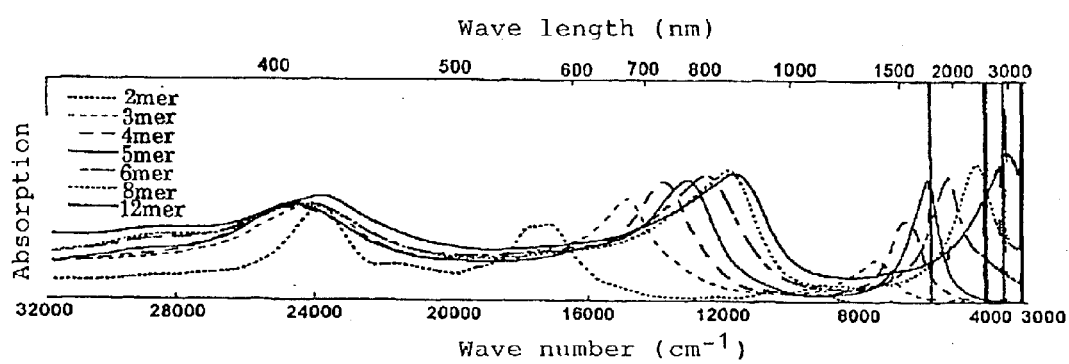
FIG. 2 shows the infrared absorption spectra of the meso-meso, β—β, β—β triply directly linked, so-called fused Zn(II) porphyrin oligomers up to 12-mer that are the present invention.

In order to confirm that the electronic absorptions of the meso-meso, β—β, β—β triply directly linked, so-called fused Zn(II) porphyrin oligomers reach into the infrared region, the infrared (IR) spectra of these the meso-meso, β—β, β—β triply directly linked, so-called fused Zn(I) porphyrin oligomers were measured in an usual KBr pellet. C—H stretching vibration is observed at 2900 $cm^{-1}$. The electronic absorption band is observed in the infrared region in the IR spectrum of the 2-mer (dimer) but the electronic absorption band is observed at 5500–6500 $cm^{-1}$ in the IR spectrum of the 3-mer, and the electronic absorption bands well enter into these IR region upon the increase of the number of the porphyrins, 4-mer, 5-mer, and 6-mer. The electronic absorption bands of 8-mer and 12-mer completely cover almost the whole IR region, thus making the C—H stretching vibration being almost undetectable.

THE BEST EMBODIMENT TO CARRY OUT THE INVENTION

The present invention will be described in more detail.

A. As the precursor for the synthesis of the meso-meso, β—β, β—β triply directly linked, so-called fused Zn(II)-porphyrin oligomers, the known meso-meso linked poryphyrin oligomers represented by the general formula 2 are used. Further, regarding to meso-meso-linked poryphyrin oligomers larger than 9-mer, the present inventor had already proposed (Japanese Patent Application 11-248756: JP Laid Open Pub. 2001-72745), can be also used as the starting material for the corresponding the mesa-mesa, β—β, β—β triply directly linked, so-called fused Zn(II) porphyrin oligomers-of the present invention. According to the specification of the said document, the corresponding polymers of the meso-meso linked porphyrins, poly (porphynylene)s that are larger than 200-mer can be easily prepared, and the reaction chromatogram of the similar polymerization reaction indicted the formation of the 300-mer to 400-mer and even higher porphyrin arrays. These very large meso-meso linked porphyrin arrays are also used as the precursor for the synthesis of the meso-meso, β—β, β—β triply directly linked, so-called fused Zn(II) porphyrin oligomers.

In the reaction claimed in this invention, the oxidation of the above meso-meso linked porphyrin oligomers with quinone oxidants in the presence of Lewis acid containing rare earth element gives the corresponding meso-meso, β—β, β—β triply directly linked, so-called fused Zn(II) porphyrin oligomers represented by general formula 3.

B. The synthetic method of the compounds of the present invention.

1. The Synthetic Method Using the Meso-Meso Linked Porphyrin Arrays Represented by the General Formula 2.

In the present reaction of the invention, carbon-carbon bonds are formed between the β-positions adjacent to the meso-meso linkage of the neighboring porphyrin rings.

So far, the present inventor has found that 5,15-diaryl metalloporphyrins and 5,10,15-triaryl metalloporphyrins which commonly have sterically uncongested peripherals are effectively coupled to metalloporphyrin dimers upon electrochemical oxidation. In these coupling reactions, the coupling regio-selectivities are dependent upon the central metal in the porphyrin core. For example, Zn(II) and Mg(II) porphyrins are coupled to form singly meso-meso bonded diporphyrins, while Ni(II), Cu(II), and Pd(II) porphyrins are coupled to form singly meso-β bonded diporphyrins, which can be further converted into mesa-β doubly linked, so-called fused coplanar diporphyrins upon oxidation with aminium cation radical of tris(para-bromopheny) aminium hexachloroamtimonate ((p-BrC$_6$H)$_3$NSbCl$_6$, BAHA).

The observed different coupling regio-selectivies, meso-meso-bonding for Zn(II) and Mg(II) porphyrins, and meso-β bonding for Cu(II), Ni(II), and Pd(II) porphyrins, can be explained in terms of the electronic structure of the intervening cation radicals. In the cases of Mg(II) and Zn(II) porphyrins, the cation radical formed upon one-electron oxidation should have an unpaired electron at $A_{2u}$ HOMO orbital, in which large spin density can be found at the meso-positions, while only negligible spin density can be found at the β-positions. On the other hand, the cation radicals formed from the one-electron oxidation of 5,15-diaryl Ni(II), and Cu(II), and Pd(II)-porphyrins should have an unpaired electron at the peripheral β-positions, while only negligible spin density can be found at the meso-positions.

These consideration leads to a conclusion that meso-meso-linked diporphyrins are from metalloporphyrin which has $A_{2u}$ HOMO bearing large density at the meso-position, while meso-β linked diporphyrins are formed from metalloporphyrin which has $A_{1u}$ HOMO bearing nodal phanes at the meso-positions and large density at the β-position. Despite these results, the present inventor has found that oxidation of meso-meso-linked Zn$^{II}$-porphyrin arrays with DDQ and Sc(OTf)$_3$ led to the formation of meso-meso, β—β, β—β triply directly linked porphyrin arrays in high yields.

2. Oxidization Procedures to Form β—β Carbon Bonds at Two β-Positions Neighboring to the Meos-Meso Linkage.

In the course of these studies on optimizing the oxidative transformation of meso-meso linked porphyrin arrays to the corresponding meso-meso, β—β, β—β triply linked porphyrin, we have found that combined use of quinone oxidant and Lewis acid containing rare earth element, for example, lanthanide triflate (trifluoromethanesulfonic acid) leads to improved coupling regio-selectivity and successful coupling of higher meso-meso linked porphyrin.

1) 2,3-dichloro-5,6-ducyano-1,4-benzoquinone (DDQ), 1,4-benzoquinone, and 2,3,5,6-tetrafluoro-1,4-benzoquinone can be mentioned as a desirable oxidant.
2) Sc, Y, La, and Eu can be mentioned as a desirable lanthanide metal.
3) Aromatic hydrocarbons such as toluene and benzonitrile can be mentioned as a desirable reaction solvent.
4) The reaction is desirably carried out under refluxing conditions in the above mentioned desirable solvent.

C. Synthetic method of meso-meso, β—β, β—β triply linked porphyrin dimers from the above mentioned 5,10,15-triaryl metalloporphyrin represented by general formula 3.

1) The fundamental conditions including oxidant, Lewis acid, solvent, and reaction temperature, are essentially the same as those of the item B.
2) Desirably, approximately 5 equivalent amounts of the quinone oxidants as well as Lewis acid are used per two newly formed β—β bonds.

EXAMPLES

Example 1

In a 50 mL flask, meso-meso-linked Zn$^{II}$-diporphyrin (18 mg, 8 μmol) was dissolved into toluene (30 mL). 2,3-Dichloro-5,6-didicyano-1,4-benzoquinone (DDQ) (9 mg, 40 μmol) and scandium trifluoromethane sulfonate Sc(CF$_3$SO$_3$)$_3$ (20 mg, 40 μmol) [often abbreviated by Sc(OTf)$_3$], were added and the resulting solution was refluxed for 1 h and was then diluted by addition of methanol and tetrahydrofuran (THF). After the solvent is removed by a rotary evaporator, the residue was dissolved into THF and was passed through an aluminum column. Then, recrystallization from a mixture of benzene and acetonitrile gave the meso-meso, β—β, β—β triply directly linked, so called fused porphyrin dimer (12.9 mg, yield; 86%).

This reaction is shown by scheme (1), in which Ar is 3,5-t-butylphenyl group.

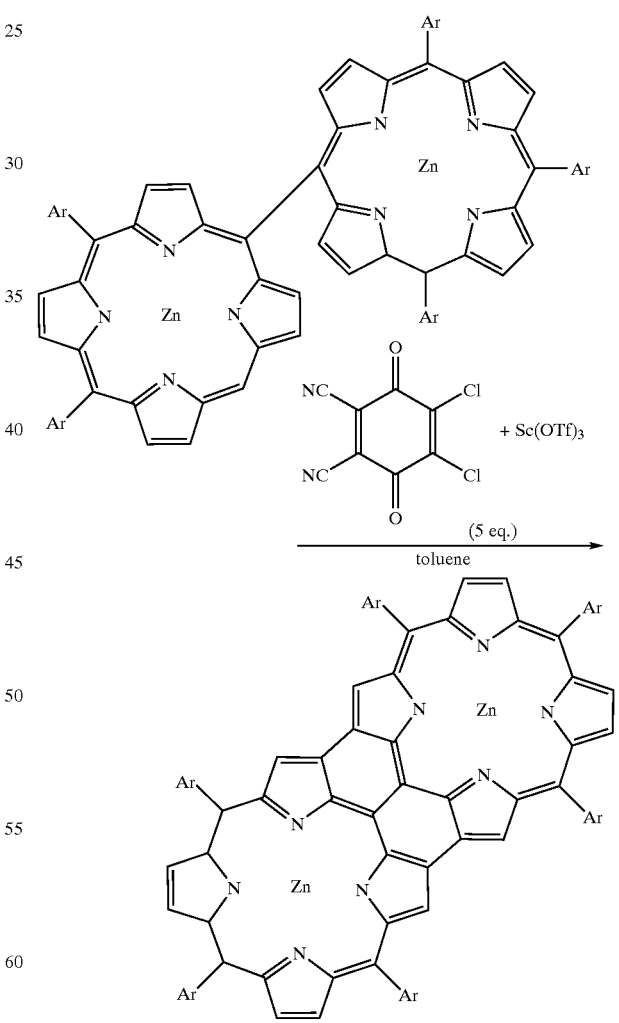

Scheme (1)

NMR: $^1$H NMR(CDCl$_3$) 1.41 (s, 36H, t-Bu), 1.45 (s, 72H, t-Bu), 7.35 (s, 4H, Por-β), 7.59 (t, J=1.8 Hz, 2H, Ar-H), 7.61 (t, J=1.8 Hz, 4H, Ar-H), 7.63 (d, J=1.8 Hz, 4H, Ar-H), 7.67(d, J=1.8 Hz, 8H, Ar-H), 7.70 (d, J=4.9 Hz, 4H, Por-β)

and 7.75 (d, J=4.9 Hz, 4H, Por-β); MALDI-TOF MS m/z= 1868, Calcd m/z for $Cl_{24}H_{138}N_8Zn_2$ is 1867; UV/Vis ($CHCl_3$): $\lambda_{max}$=419(Soret), 582(Soret), and 1068 nm.

It is noted here that the previous preparation of the similar fused porphyrin dimer using meso-meso linked $Cu^{II}$-diporphyrin (Patent Laid open Publication 2000-110157) was achieved at best in 82% yield. In the reaction of scheme 1, the yields of the fused porphyrin dimer and the recovery of the starting meso-meso linked diporphyrin are summarized in Table 1, where several quinone oxidants and lanthanide triflate were tested, with changing reaction time.

TABLE 1

| No. | Solvent | Time | Quinone | Equivalent value | Lewis acid | Equivalent value | Yield (%) 2 | 1 recoverd |
|---|---|---|---|---|---|---|---|---|
| 1 | Toluene | 0.5 | DDQ | 5 | $Sc(OTf)_3$ | 5 | 86 | 0 |
| 2 | Toluene | 1 | DDQ | 2.2 | $Sc(OTf)_3$ | 2.2 | 87 | 10 |
| 3 | Toluene | 12 | DDQ | 5 | $Y(OTf)_3$ | 5 | 20 | 68 |
| 4 | Toluene | 24 | DDQ | 5 | $La(OTf)_3$ | 5 | 16 | 80 |
| 5 | Toluene | 24 | DDQ | 5 | $Eu(OTf)_3$ | 5 | 9 | 75 |
| 6 | Toluene | 36 | DDQ | 5 | $Mg(OTf)_3$ | 5 | 0 | 74 |
| 7 | Toluene | 20 | p-benzo quinone | 5 | $Sc(OTf)_3$ | 5 | 56 | 20 |
| 8 | Toluene | 20 | Fluoranile | 5 | $Sc(OTf)_3$ | 5 | 67 | 27 |
| 9 | THF | 10 | DDQ | 5 | $Sc(OTf)_3$ | 5 | 0 | 96 |
| 10 | Benzo-nitrile | 0.5 | DDQ | 5 | $Sc(OTf)_3$ | 5 | 35 | 0 |
| 11 | Toluene | 20 | DDQ | 5 | — | — | 0 | 80 |
| 12 | Toluene | 20 | — | — | $Sc(OTf)_3$ | 5 | 0 | 96 |

The results of Table 1 indicate that the reacting solvent, reacting time (refluxing time), the oxidizing agent (concentration) and lanthanide Lewis acid (concentration) are all important parameters for the synthesis of the meso-meso, β—β, β—β triply directly linked porphyrin dimmer of the present invention.

Furthermore, the results of Example 1 suggest that this oxidative ring closuring reaction can be applied to mono-disperse longer meso-meso linked porphyrin oligomers bearing the end, end-bisphensyl caps, which can be easily prepared from the meso-meso linked mono-disperse porphyrin arrays, which have been reported by the present inventor (Japanese Patent Application 11-248756).

Example 2

In a round 50 mL flask, end, end-diphenyl-substituted meso-meso-linked Zn(II)-hexaporphyrin (30 mg, 4.7 μmol) was dissolved into toluene (50 mL). DDQ (27 mg, 119 μmol) and $Sc(OTf)_3$ (59 mg, 119 μmol) were added and the resulting mixture was refluxed for 2 h and was then diluted by addition of methanol and THF. The solvent was removed by a rotary evaporator and the residue was dissolved into THF and was passed through an aluminum column. Then, recrystallization from a mixture of benzene and acetonitrile gave the target meso-meso, β—β, β—β triply directly linked porphyrin hexamer (18.5 mg, yield; 62%). UV-vis($CHCl_3$): $\lambda_{max}$=448 (Soret), 876 (Soret) and 1892 nm.

Example 3

To a solution of 5,10,15-tris(3,5-ditertbutylphneyl) substituted Zn(II) porphyrin (30 mg, 32 μmol) in toluene (50 mL) were added DDQ (36 mg, 160 μmol) and $Sc(OTf)_3$ (79 mg, 160 μmol). The resulting solution was refluxed for 5 h and was then diluted by addition of methanol and THF. The solvent was removed by a rotary evaporator and the residue was dissolved into THF and was passed through an aluminum column. Then, recrystallization from a mixture of benzene and acetonitrile gave the target meso-meso, β—β, β—β triply directly linked porphyrin dimer (27 mg, yield; 90%). UV-vis($CHCl_3$): $\lambda$max=448 (Soret), 876 (Soret) and 1892 nm.

This oxidative dimerization reaction is indicated by scheme (2), in which Ar are all 3,5-t-butylphenyl group.

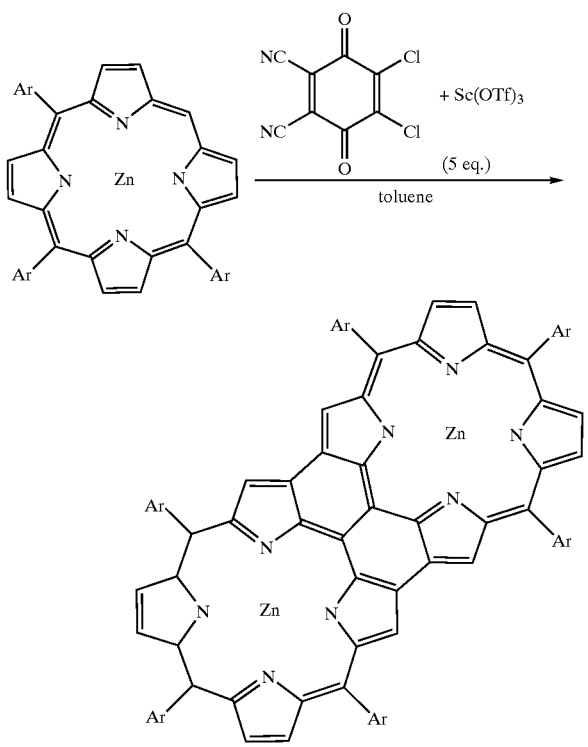

Scheme 2

In FIG. 1, the absorption spectra of the meso-meso, β—β, β—β triply directly linked porphyrin oligomer (2-mer, 3-mer, 4-mer, 5-mer, 6-mer, 8-mer, and 12-mer) synthesized in the present invention are shown, clearly indicating that the electronic absorption of these conjugated porphyrin arrays reach into well the IR region at 2600–2700 cm$^{-1}$.

The most red-shifted electronic absorption bands of meso-meso, β—β, β—β triply directly linked Zn(II) porphyrin oligomers are at 9400 cm$^{-1}$ (2-mer), 7500 cm$^{-1}$ (3-mer), 6600 cm$^{-1}$ (4-mer), 6000 cm$^{-1}$ (5-mer), 5400 cm$^{-1}$ (6-mer), 4500 cm$^{-1}$ (8-mer), 3500 cm$^{-1}$ (12-mer), respectively,. The one-electron oxidation potentials (versus AgClO$_4$/Ag) have been determined to be 212 mV (2-mer), 14 mV (3-mer), −89 mV (4-mer), −147 mV (5-mer), −180 (6-mer), −241 mV (8-mer), indicating the progressive decrease with the increase of the number of porphyrins in the arrays. Both the results indicate that the electronic interactions between the porphyrin in the fused porphyrin arrays are remarkably large and even enhanced upon the increase in the number of the porphyrins. Ant thus it may be predicted that these effect will be much more enhanced in higher porphyrin arrays. These properties are also dependent upon the central metal in the porphyrin core, and therefore the metallated fused porphyrin arrays except the Zn(II) will be also fascinating target.

Industrial Applicability

As described above, the meso-meso, β—β, β—β triply directly linked porphyrin arrays are quite interesting as nonlinear optical materials, optical limiting materials, and molecular module of the electronic molecular devices in light of their very low one-electron oxidation potentials as well as their exceptionally red-shifted electronic absorption bands. The quite π-conjugated electronic systems of these fused porphyrin arrays are also interesting from a view of their application to ferromagnetic materials.

What is claimed is:

1. A Meso-meso, β—β, β—β triply directly linked fused porphyrin discrete oligomer represented by formula 1, formula 1

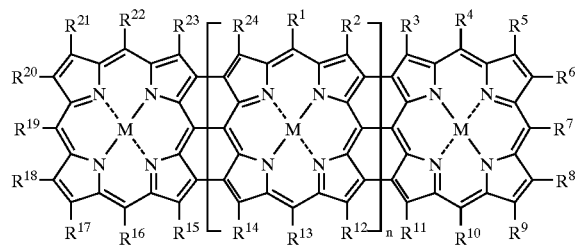

wherein, $R^1$–$R^{24}$ are selected independently from the group consisting of hydrogen, halogen, hydroxyl group, mercapto group, amino group, nitro group, cyano group, carboxyl group, sulfonic acid group, substituted or nonsubstituted alkyl group, substituted or non-substituted aryl group, substituted or non-substituted alkoxy group, substituted or non-substituted aryloxy group, substituted or non-substituted alkylthio group, substituted or non-substituted arylthio group, alkylamino group, substituted or non-substituted arylamino group, substituted or non-substituted carboxylate group, substituted or non-substituted carboxylic acid amino group, substituted or non-substituted sulfonate group, substituted or non-substituted sulfonamide group, substituted or non-substituted carbonyl group, substituted or non-substituted silyl group or substituted or non-substituted siloxy group, where $2 \leq n \leq 400$ M is 2H or a metal atom selected from the group consisting of Zn, Mg, Ca, Sr, Ba, Sc, Y, La, Ce, Pr, Nd, Sm, Eu, Gd, Tb, Dy, Ho, Er, Tm, Yb, Lu, Ti, Zr, Hf, V, Nb, Ta, Th, U, Cr, Mo, W, Mn, Tc, Re, Fe, Ru, Os, Co, Rh, Ir, Ni, Pd, Pt, Cu, Ag, Au, Cd, Hg, Al, Ga, In, Ti, Si, Ge, Sn, Pb, As, Sb, and Bi.

2. The meso-meso, β—β, β—β triply directly linked, fused porphyrin discrete oligomer of claim 1, wherein in formula 1, $R^1$, $R^4$, $R^{10}$, $R^{13}$, $R^{16}$, $R^{22}$ are selected independently from phenyl groups having substituents selected independently from alkyl group or alkoxy group of carbon number 1 or more, $R^7$ and $R^{19}$ are selected independently from the group consisting of hydrogen, halogen, hydroxyl group, mercapto group, amino group, nitro group, cyano group, carboxyl group, sulfonic acid group, substituted or non-substituted alkyl group, substituted or non-substituted aryl group, substituted or non-substituted alkoxy group, substituted or non-substituted aryloxy group, substituted or non-substituted alkylthio group, substituted or non-substituted arylthio group, alkylamino group, substituted or non-substituted arylamino group, substituted or non-substituted carboxylate group, substituted or non-substituted carboxylic acid amino group, substituted or non-substituted sulfonate group, substituted or non-substituted sulfonamide group, substituted or non-substituted carbonyl group, substituted or non-substituted silyl group or substituted or non-substituted siloxy group.

3. The meso-meso, β—β, β—β, triply directly linked fused porphyrin oligomer of claim 1, wherein $R^1$, $R^4$, $R^{10}$, $R^{13}$, $R^{16}$ and $R^{22}$ are independently selected from the group consisting of 3,5-di-terbutylphenyl and 3, 5-di-octyloxyphenyl groups.

4. A method for synthesizing a fused M(+m)-porphyrin compound comprising the steps of:

(1) synthesizing a Zn(II)-porphyrin compound represented by formula 1, formula 1

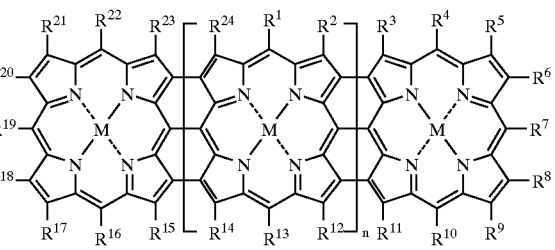

wherein M is Zn, formed by fusing a Zn(II)-porphyrin represented by formula 2 in a solvent under the presence of guinone, which is an oxidizing agent, and a Lewis acid containing rare earth element,

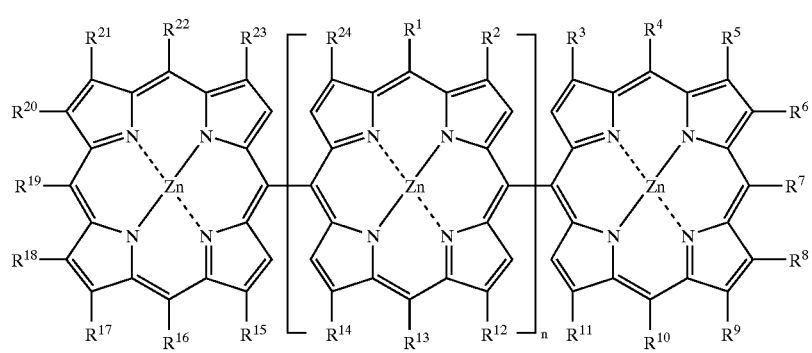

General formula 2 wherein $R^1$–$R^{24}$ are selected independently from the group consisting of hydrogen, halogen, hydroxyl group, mercapto group, amino group, nitro group, cyano group, carboxyl group, sulfonic acid group, substituted or non-substituted alkyl group, substituted or non-substituted aryl group, substituted or non-substituted alkoxy group, substituted or non-substituted aryloxy group, substituted or non-substituted alkylthio group, substituted or non-substituted arylthio group, alkylamino group, substituted or non-substituted arylamino group, substituted or non-substituted carboxylate group, substituted or non-substituted carboxylic acid amino group, substituted or non-substituted sulfonate group, substituted or non-substituted sulfonamide group, substituted or non-substituted carbonyl group, substituted or non-substituted silyl group or substituted or non-substituted siloxy group, where $2 \leq n \leq 400$ each Zn(II)-porphyrin ring being triply linked with two β—β carbon bonds and one meso carbon bond, (2) forming a fused porphyrin compound having a M of 2H by demetalization of Zn from the Zn(II)-porphyrin compound obtained in step (1), and (3) forming the fused M(+m)-porphyrin compound by inserting a metal other than Zn for M wherein M is selected from the group consisting of Mg, Ca, Sr, Ba, Sc, Y, La, Ce, Pr, Nd, Sm, Eu, Gd, Tb, Dy, Ho, Er, Tm, Yb, Lu, Ti, Zr, Hf, V, Nb, Ta, Th, U, Cr, Mo, W, Mn, Tc, Re, Fe, Ru, Os, Co, Rh, Ir, Ni, Pd, Pt, Cu, Ag, Au, Cd, Hg, Al, Ga, In, Tl, Si, Ge, Sn, Pb, As, Sb, and Bi, and m is an ionic valency number of each metal.

5. The method for synthesizing the fused Zn(II)-porphyrin compound of claim 4, wherein $R^1$, $R^4$, $R^7$, $R^{10}$, $R^{13}$, $R^{16}$, $R^{19}$ and $R^{22}$ of formula 2 are a phenyl group or a substituted phenyl group having a substituent selected independently from alkyl group or alkoxy group of carbon number 1 or more.

6. The method for synthesizing the fused Zn(II)-porphyrin compound of claim 5 further comprising the step of:

carrying out step (1) by reflux using an aromatic hydrocarbon solvent containing an oxidizing agent selected from guinines, and Lewis acid containing rare earth element.

7. A method for synthesizing a fused M(+m)-porphyrin comprising the steps of:

(1) fusing a Zn(II)-porphyrin represented by formula 3,

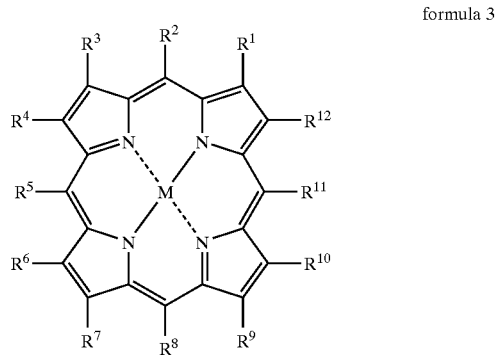

formula 3 wherein, M is Zn, $R^{10}$–$R^{12}$ are hydrogen and $R^1$–$R^9$ are selected independently from the group consisting of hydrogen, halogen, hydroxyl group, mercapto group, amino group, nitro group, cyano group, carboxyl group, sulfonic acid group, substituted or non-substituted alkyl group, substituted or non-substituted aryl group, substituted or non-substituted alkoxy group, substituted or non-substituted aryloxy group, substituted or non-substituted alkythio group, substituted or non-substituted arylthio group, alkylamino group, substituted or non-substituted arylamino group, substituted or non-substituted carboxylate group, substituted or non-substituted carboxylic acid amino group, substituted or non-substituted sulfonate group, substituted or non-substituted sulfonamide group, substituted or non-substituted carbonyl group, substituted or non-substituted silyl group or substituted or non-substituted siloxy group, in the solvent under the presence of quinone, which is an oxidizing agent, and Lewis acid containing rare earth element, each Zn(II)-porphyrin ring being triply linked with two β—β carbon bonds and one meso carbon bond, (2) forming a fused porphyrin compound having a M of 2H by demetalization of Zn from the Zn(II)-porphyrin compound obtained in step (1), and (3) forming the fused M(+m)-porphyrin compound by inserting a metal other than Zn for M wherein M is selected from the group consisting of Mg, Ca, Sr, Ba, Sc, Y, La, Ce, Pr, Nd, Sm, Eu, Gd, Tb, Dy, Ho, Er, Tm, Yb, Lu, Tl, Zr, Hf, V, Nb, Ta, Th, U, Cr, Mo, W, Mn, Tc, Re, Fe, Ru, Os, Co, Rh, Ir, Ni, Pd, Pt, Cu, Ag, Au, Cd, Hg, Al, Ga, In, Ti, Si, Ge, Sn, Pb, As, Sb, and Bi, and m is an ionic valency number of each metal.

8. The method for synthesizing the fused Zn(II)-porphyrin compound of claim 7, comprising the steps of:

using the Zn(II)-porphyrin compound of formula 3, wherein, $R^1$, $R^3$, $R^4$, $R^6$, $R^7$, $R^9$–$R^{12}$ are hydrogen, $R^2$, $R^5$ and $R^8$ are a phenyl group having substituent selected independently from alkyl group or alkoxy group of carbon number 1 or more.

9. The method for synthesizing the fused Zn(II)-porphyrin compound of claim 8, wherein the phenyl group having substituent selected independently from alkyl group or alkoxy group of carbon number 1 or more in formula 3, is a phenyl group whose 3, 5 positions are substituted by tertiary butyl group or octyloxi group.

10. The method for synthesizing the fused Zn(II)-porphyrin compound of claim 9, further comprising the step of:

carrying out the step (1) by reflux using an aromatic hydro carbon solvent containing an oxidizing agent selected from guinines, and Lewis acid containing rare earth element.

* * * * *